US009820515B2

(12) United States Patent
Crockett, Jr.

(10) Patent No.: US 9,820,515 B2
(45) Date of Patent: Nov. 21, 2017

(54) APPAREL WITH THERMOCHROMIC DYES FOR MONITORING AND OPTIMIZING EXERCISE PERFORMANCE

(71) Applicant: Kenneth E. Crockett, Jr., West Chester, PA (US)

(72) Inventor: Kenneth E. Crockett, Jr., West Chester, PA (US)

(*) Notice: Subject to any disclaimer, the term of this patent is extended or adjusted under 35 U.S.C. 154(b) by 900 days.

(21) Appl. No.: 13/833,427

(22) Filed: Mar. 15, 2013

(65) Prior Publication Data

US 2013/0263352 A1 Oct. 10, 2013

Related U.S. Application Data

(60) Provisional application No. 61/621,066, filed on Apr. 6, 2012.

(51) Int. Cl.
*A41D 13/00* (2006.01)
*A61B 5/01* (2006.01)
*A63B 71/06* (2006.01)
*A61B 5/00* (2006.01)

(52) U.S. Cl.
CPC ............ *A41D 13/0015* (2013.01); *A61B 5/01* (2013.01); *A61B 5/6805* (2013.01); *A63B 71/06* (2013.01); *A61B 2562/0276* (2013.01)

(58) Field of Classification Search
CPC ................ G01K 11/12; A41D 19/0027; A41D 13/1281
See application file for complete search history.

(56) References Cited

U.S. PATENT DOCUMENTS

| | | | | |
|---|---|---|---|---|
| 4,028,118 A | * | 6/1977 | Nakasuji | C08K 5/0041 106/31.19 |
| 4,642,250 A | * | 2/1987 | Spector | A41D 31/00 374/E11.022 |
| 4,681,791 A | * | 7/1987 | Shibahashi | B41M 5/287 374/E11.021 |
| 4,717,710 A | * | 1/1988 | Shimizu | C09K 9/02 106/311 |

(Continued)

FOREIGN PATENT DOCUMENTS

| | | |
|---|---|---|
| EP | 0645489 | 3/1995 |
| EP | 0751010 | 1/1997 |

(Continued)

OTHER PUBLICATIONS

Search Report received in counterpart United Kingdom Patent Application No. GB1317597.1 dated Mar. 12, 2014.

(Continued)

*Primary Examiner* — Richale Quinn
(74) *Attorney, Agent, or Firm* — Pryor Cashman LLP (57) ABSTRACT

Apparel for monitoring optimal body shell temperature during physical activity. The apparel uses thermochromic dyes and thermochromic inks to indicate changes in body shell temperature as physical activity commences and progresses. The thermochromic dyes and inks reveal when the body shell temperature has reached a temperature indicating optimal muscle performance, and inform the wearer of the apparel whether to increase or decrease the intensity of the physical activity to establish or maintain the optimal body shell temperature.

17 Claims, 3 Drawing Sheets

(56) References Cited

U.S. PATENT DOCUMENTS

| | | | |
|---|---|---|---|
| 4,725,462 A * | 2/1988 | Kimura | A63H 3/02 283/97 |
| 5,124,819 A * | 6/1992 | Davis | G01K 11/165 349/199 |
| 5,202,677 A * | 4/1993 | Parker | G02F 1/0147 349/161 |
| 5,221,288 A | 6/1993 | Kamata et al. | |
| 5,558,700 A | 9/1996 | Shibahashi et al. | |
| 6,188,506 B1 * | 2/2001 | Kaiserman | B44F 1/08 359/288 |
| 6,196,241 B1 * | 3/2001 | Doolan | A45B 25/18 135/16 |
| 6,228,804 B1 | 5/2001 | Nakashima | |
| 6,416,853 B1 * | 7/2002 | Nakashima | A63H 33/22 428/29 |
| 6,712,996 B2 * | 3/2004 | Wu | G01K 11/14 252/408.1 |
| 6,990,688 B2 | 1/2006 | Aperfine et al. | |
| 7,258,073 B2 * | 8/2007 | McGuire | G01K 11/12 116/216 |
| 7,674,747 B1 * | 3/2010 | Long | D06P 1/004 503/201 |
| 8,029,190 B2 * | 10/2011 | MacDonald | A41D 13/002 116/216 |
| 8,038,446 B2 * | 10/2011 | Cohen | G09B 19/0076 434/247 |
| 8,182,430 B2 * | 5/2012 | Short | G01K 11/14 374/162 |
| D664,739 S * | 8/2012 | Gibson | D2/840 |
| 8,435,924 B2 * | 5/2013 | Arora | A61F 13/15699 430/270.1 |
| 8,754,005 B2 * | 6/2014 | Gil | C09D 11/50 106/31.32 |
| 2002/0137417 A1 * | 9/2002 | Tebbe | D06H 1/00 442/130 |
| 2003/0224155 A1 | 12/2003 | Orth et al. | |
| 2004/0158156 A1 | 8/2004 | Schneemeyer et al. | |
| 2006/0023292 A1 * | 2/2006 | Simone, Jr. | G09F 21/02 359/288 |
| 2006/0287215 A1 | 12/2006 | McDonald et al. | |
| 2008/0279253 A1 * | 11/2008 | MacDonald | A41D 13/002 374/162 |
| 2008/0289535 A1 * | 11/2008 | Spector | D06P 1/004 106/31.13 |
| 2009/0046760 A1 | 2/2009 | Matheson | |
| 2009/0143516 A1 * | 6/2009 | MacDonald | A61B 5/015 524/236 |
| 2010/0012017 A1 * | 1/2010 | Miller | A61B 5/015 116/201 |
| 2010/0251454 A1 * | 10/2010 | Kiernan | A41D 1/002 2/69 |
| 2010/0268112 A1 * | 10/2010 | Short | G01K 11/16 600/549 |
| 2010/0313325 A1 * | 12/2010 | Ebejer | A41B 13/005 2/80 |
| 2011/0035878 A1 | 2/2011 | Rouse | |
| 2012/0130268 A1 * | 5/2012 | Fayed | A61F 13/42 600/549 |
| 2013/0177216 A1 * | 7/2013 | Shuster | G06K 9/62 382/111 |
| 2014/0245527 A1 * | 9/2014 | Douglas | A41D 13/0051 2/459 |
| 2014/0366238 A1 * | 12/2014 | Owen | A41D 13/0015 2/69 |
| 2015/0366504 A1 * | 12/2015 | Connor | A61B 5/6804 600/301 |

FOREIGN PATENT DOCUMENTS

| | | |
|---|---|---|
| WO | 2007125439 | 11/2007 |
| WO | 2008115682 | 9/2008 |
| WO | 2009095633 | 8/2009 |

OTHER PUBLICATIONS

Periyasamy, S., et al., "Thermochromic colors in textiles", Colourage, vol. 55, No. 2, (2008) pp. 53-62.

Wallace, Kerri, "Wear it well", Made Magazine, Issue 3.09, Sep. 2009, pp. 28-30.

* cited by examiner

APPAREL WITH THERMOCHROMIC DYES FOR MONITORING AND OPTIMIZING EXERCISE PERFORMANCE

CROSS REFERENCE TO RELATED APPLICATIONS

This application claims priority to U.S. Provisional Application No. 61/621,066, filed on Apr. 6, 2012, the contents of which are incorporated by reference herein, in their entirety and for all purposes.

FIELD OF THE INVENTION

The invention relates generally to textiles, and in particular, to exercise apparel including a plurality of thermochromic dyes that indicate optimal muscle performance and which also may warn of hyperthermic muscle conditions, including a hyperthermic core body temperature reflected in an elevated body shell temperature.

BACKGROUND OF THE INVENTION

Fitness apparel provides comfort to the athlete, and allows the athlete to exercise in different climates and conditions. Modern iterations of such apparel also wick moisture away from the skin. But the fabrics from which fitness apparel is produced do not inform the wearer or trainer of the body's condition during exercise. For example, the fabrics do not provide information about the body's temperature, caloric burn, or peak performance. Rather, to the extent the athlete or trainer needs to have such information, they generally must rely on electronic sensors or their own assessment concerning how the body is performing.

Thermochromic pigments have pervaded many facets of daily activities. These pigments, which have been formulated as inks and dyes, have also been used in articles of clothing, primarily for aesthetic purposes. Thermochromically colored articles of clothing have not included thermochromic inks and dyes that change color in a more precise range of temperature, for example, for temperature and muscle performance monitoring.

A need exists for athletes to monitor and enhance their performance in an economical manner, particularly for casual or amateur athletes. Temperature monitoring may go a long way toward performance optimization.

SUMMARY OF THE INVENTION

The invention features apparel for monitoring optimal body shell temperature in a wearer of the apparel. The apparel may find use, for example, in temperature monitoring by athletes, as well as in medical temperature monitoring indications. The temperature monitoring may reveal a hyperthermic condition.

In some aspects, the apparel comprises a moisture-wicking fabric, which may comprise cotton, nylon, polyester, or blends thereof. In some aspects, the apparel comprises a plurality of thermochromic dyes. The apparel may comprise a first thermochromic dye that changes color at about 32 degrees C., a second thermochromic dye that changes color at about 34 degrees C., and a third thermochromic dye that changes color at about 36 degrees C. The apparel may comprise a first thermochromic dye that changes color at about 33 degrees C., a second thermochromic dye that changes color at about 35 degrees C., and a third thermochromic dye that changes color at about 37 degrees C.

Optionally, the apparel may comprise a logo or a design comprising a thermochromic ink that changes color at about 33 degrees C., at about 34 degrees C., or at about 35 degrees C. Optionally, the apparel may comprise a fourth thermochromic dye that changes color at about 37 degrees C., or that changes color at about 38 degrees C., or that changes color at about 39 degrees C., or that changes color at about 40 degrees C.

The apparel preferably comprises a shirt. The shirt may comprise the plurality of thermochromic dyes, including the first, second, third, and fourth thermochromic dyes only in the sleeves, or only in the shoulder portion of the shirt, or only the front of the shirt, or only the back of the shirt, or only in the chest portion of the shirt, or only in the abdominal portion of the shirt, or combinations thereof.

The apparel may be used in a method of monitoring optimal muscle performance during physical activity in a subject wearing the apparel. In some aspects, the methods include the steps of exercising one or more muscle groups beneath the apparel to a degree that increases the body shell temperature between the muscle groups and the apparel, determining the body shell temperature is at least 32 degrees C. by detecting a change from a first color of the apparel to a second color of the apparel, and increasing the intensity of the exercise of the one or more muscle groups to a degree that increases the body shell temperature between the muscle groups and the apparel until the body shell temperature is at least 34 degrees C., and determining the body shell temperature is at least 34 degrees C. by detecting a change from the color of the apparel to a third color of the apparel. In some aspects, the methods include the steps of exercising one or more muscle groups beneath the apparel to a degree that increases the body shell temperature between the muscle groups and the apparel, determining the body shell temperature is at least 33 degrees C. by detecting a change from a first color of the apparel to a second color of the apparel, and increasing the intensity of the exercise of the one or more muscle groups to a degree that increases the body shell temperature between the muscle groups and the apparel until the body shell temperature is at least 35 degrees C., and determining the body shell temperature is at least 35 degrees C. by detecting a change from the color of the apparel to a third color of the apparel.

The methods may further comprise determining the body shell temperature is at least 36 degrees by detecting a change from the third color of the apparel to a fourth color of the apparel, and decreasing the intensity of the exercise of the one or more muscle groups to a degree that decreases the body shell temperature between the muscle groups and the apparel until the body shell temperature is at least 34 degrees C. The methods may further comprise determining the body shell temperature is at least 37 degrees by detecting a change from the third color of the apparel to a fourth color of the apparel, and decreasing the intensity of the exercise of the one or more muscle groups to a degree that decreases the body shell temperature between the muscle groups and the apparel until the body shell temperature is at least 35 degrees C.

The invention also provides a method for coloring moisture-wicking apparel with a plurality of thermochromic dyes. The method generally comprises the steps of contacting apparel with a cationic agent for a period of time sufficient to confer a charge on the fabric of the apparel, rinsing the apparel to remove the cationic agent, contacting the apparel with a dye solution comprising a first thermochromic dye that changes color at about 32 degrees C., a second thermochromic dye that changes color at about 34 degrees C., and a third thermochromic dye that changes color at about 36 degrees C. for a period of time sufficient to color the fabric, or with a dye solution comprising a first thermochromic dye that changes color at about 33 degrees C., a second thermochromic dye that changes color at about 35 degrees C., and a third thermochromic dye that changes color at about 37 degrees C. for a period of time sufficient to color the fabric, adding a dispersing agent to the dye solution and contacting the apparel with the dispersing agent for a period of time sufficient to substantially uniformly coat the thermochromic dyes onto the fabric, adding a fixing agent to the dye solution and contacting the apparel with the fixing agent for a period of time sufficient to fix the thermochromic dyes to the fibers, adding a binding agent to the dye solution and contacting the apparel with the binding agent for a period of time sufficient to bind the thermochromic dyes to the fibers, rinsing the apparel to remove the dye solution, drying the apparel, and optionally, coating a logo or a design onto the apparel with a thermochromic ink that changes color at about 34 degrees C. or that changes color at about 35 degrees C.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms "comprising" and "including" encompass the more restrictive terms "consisting essentially of" and "consisting of."

The invention features apparel for determining optimal and suboptimal muscle performance during exercise, reflected in body surface heat changes that mediate color changes in thermochromic inks and dyes impregnated in or coated on the fibers of the apparel. The invention also features methods for producing such exercise apparel, and methods for evaluating muscle performance during exercise based on body surface temperature changes. A foundational feature is mixture of thermochromic dyes and inks that change color at particular body surface temperature changes to reflect sub-optimal and optimal muscle performance, or to reflect a hyperthermic condition.

The apparel may be any article of clothing, jersey, or textile, and preferably is clothing that is intended for use during exercise, although in some aspects, the clothing may be intended for use in monitoring for a hyperthermic body shell temperature, including for medical purposes. The apparel may be an article of clothing that is typically worn during particular types of exercise or a particular sport, including running apparel, weight lifting apparel, fitness walking apparel, skiing (downhill or cross-country) apparel, bicycling apparel, swimming apparel, cross-training apparel, hiking apparel, yoga apparel, and other types of athletic clothing. Apparel includes, but is not limited to, shirts, gowns, wrist bands, shorts, pants, leggings, socks, shoes, sneakers, gloves, hats, visors, head bands, and variations or combinations thereof. Shirts are preferred.

The apparel may be fabricated from any suitable materials or fibers. The apparel may be fabricated from cotton, polyester, nylon, wool, cellulose, rayon, lyocell, elastane, spandex, silk, and combinations thereof. The apparel may have moisture-wicking, or moisture-absorbent properties. Cotton apparel is preferred in some aspects.

The apparel preferably comprises a plurality of thermochromic dyes. The thermochromic dyes may be impregnated or infused within the fibers of the material used to fabricate the apparel, or the dyes may be coated onto the surface of the fibers. The fibers of the apparel may be colored with the thermochromic dyes alone, or may be colored with a combination of thermochromic dyes and regular, non-thermochromic dyes. In cases where thermochromic dyes and regular dyes are both used, each dye type may independently be impregnated or infused within the fibers of the material used to fabricate the apparel, coated onto the surface of the fibers, or both. For example, in some aspects, the fibers are impregnated with regular, non-thermochromic dyes and are coated with the thermochromic dyes. In some aspects, the fibers are coated with both non-thermochromic and thermochromic dyes.

Figure 1:
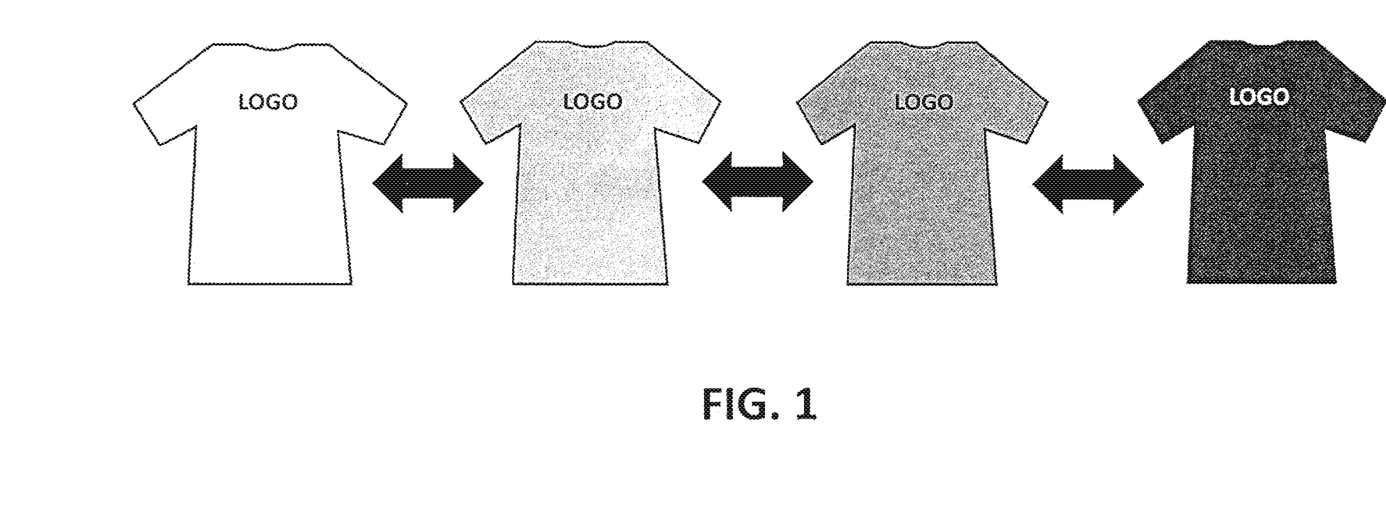
FIG. 1 diagrams a shirt color change in response to changes in surface body temperature from optimal caloric burn and muscle metabolism. The shirt changes color along a predetermined temperature continuum as each temperature along the continuum is reached, and is represented as increasing darkness of the shading in the image. The color change is reversible based on increasing and decreasing temperature.

In some aspects, the apparel further comprises at least one, or a plurality of thermochromic inks, including thermochromic paints. Thus, in addition to the fibers of the apparel comprising thermochromic dyes, the fibers may be coated with thermochromic inks. Thermochromic ink coatings may be applied to all or a portion of the apparel. For example, apparel comprising a thermochromic dye may also comprise a design, including a logo, that has been coated onto the surface of the fibers using one or a plurality of thermochromic inks. See, e.g., FIG. 1. The thermochromic ink coating may mask a portion of the apparel such that a color change of the thermochromic dyes at the portion covered by the ink would not be visible because the ink overlays the dye.

Thermochromic pigments change color in response to changes in their microenvironment, typically pH changes. Generally, the pigments toggle between a colored and colorless state. Thermochromic dyes and inks are generally packaged together with proton-donor acidic color developers and a low-melting wax, all of which are contained within a polymeric capsule or microcapsule. In the presence of the acidic color developer, the thermochromic dye is protonated from protons donated by the color developer, and the protonation causes a conformational change in the dye molecule that results in the color change. In the absence of the acidic color developer, the thermochromic dye molecule reverts to its native form and the color change is reversed. This color change may be controlled, for example, according to the melting point of the wax, such that when the wax is in solid form, the dye and acidic color developer are segregated and the first color is visible, and when the wax melts, the dye and acidic color developer may interact such that the color change occurs, and the second color is visible, or the first color becomes colorless. Thus, color changes may be controlled according to the temperature at which the wax melts. In accordance with the invention, the thermochromic dyes preferably include waxes that melt substantially at a desired temperature so that more precise temperature monitoring may be achieved.

In accordance with the invention, any suitable thermochromic dye may be used. Such dyes may comprise a leuco dye. Such dyes may comprise a liquid crystal dye. Such dyes may comprise a mixture of a lueco dye and a liquid crystal dye. The dyes may comprise a fluoran or crystal violet lactone. The dyes may comprise a red, orange, yellow, green, blue, or purple color, including any shade thereof. The dyes may be supplied in liquid, semi-liquid, slurry, or solid form.

The apparel preferably comprises a plurality of thermochromic dyes that independently change color at a particular temperature. Each of the plurality of thermochromic dyes may be selected to change or lose color at specific points along a temperature continuum, thereby exposing the next thermochromic dye color until a high enough temperature is reached and no further color changes are possible, for example, the temperature limit of the thermochromic dyes present in or on the apparel.

As the body surface/shell temperature increases, the low melting wax segregating the first thermochromic dye from its acidic developer melts, allowing the first dye and developer to interact, causing the first dye to become colorless, and thereby exposing the color of the second thermochromic dye. As the body surface temperature further increases, the wax segregating the second thermochromic dye from its acidic developer melts, allowing the second dye and developer to interact, causing the second dye to become colorless, and thereby exposing the color of the third thermochromic dye. This general reaction may progress through each of the thermochromic dyes present in the plurality of thermochromic dyes, until the last thermochromic dye has changed or lost its color. See, FIG. 1. In some aspects, when the last thermochromic dye has lost its color, a base color of the apparel, established by a non-thermochromic dye, is exposed. As the body surface temperature decreases, these reactions are reversed, and each thermochromic dye that changed color will revert to its original color. As each thermochromic dye successively reverts to its original color, the color of the apparel changes in reverse order, for example, exposing the color of the second thermochromic dye, and then the color of the first thermochromic dye.

The apparel may comprise two, three, four, five, six, seven, eight, nine, ten, or more thermochromic dyes. In preferred aspects, the apparel comprises two to five thermochromic dyes. In some aspects, the apparel comprises two to four thermochromic dyes. In some aspects, the apparel comprises three to four thermochromic dyes. In some aspects, the apparel comprises two to three thermochromic dyes.

Preferably, none of the thermochromic dyes or thermochromic inks in or on the apparel change temperature at a resting body shell temperature, such as the body shell temperature before exercise activity commences or a normal body shell temperature. Thus, at a pre-exercise, resting body shell temperature, the apparel comprises a first color, and this color will not change unless the apparel is heated to a temperature above the pre-exercise, resting body shell temperature. Such heat is supplied by the skin that is in contact with or proximal to the apparel material. The pre-exercise, resting body shell temperature may be about 29° C. to about 35° C., in some aspects may be about 29° C. to about 31° C., in some aspects may be about 30° C. to about 32° C., in some aspects may be about 30° C. to about 33° C., in some aspects may be about 31° C. to about 33° C., and in some aspects may be about 32° C. to about 34° C. Thus, in some aspects, none of the thermochromic dyes or inks will change color at a temperature not exceeding about 29° C. In some aspects, none of the thermochromic dyes or inks will change color at a temperature not exceeding about 30° C. In some aspects, none of the thermochromic dyes or inks will change color at a temperature not exceeding about 31° C. In some aspects, none of the thermochromic dyes or inks will change color at a temperature not exceeding about 32° C. In some aspects, none of the thermochromic dyes or inks will change color at a temperature not exceeding about 33° C. In some aspects, none of the thermochromic dyes or inks will change color at a temperature not exceeding about 34° C. In some aspects, none of the thermochromic dyes or inks will change color at a temperature not exceeding about 35° C.

The additional thermochromic dyes and inks change color when the apparel is heated to a temperature above the pre-exercise, resting body shell temperature. Such dyes and inks may change color, including loss of color, at a temperature that is preferably greater than about 32° C., in some aspects, greater than about 33° C., in some aspects, greater than about 34° C., and in some aspects, greater than about 35° C. Second, third, fourth, fifth, and additional thermochromic dyes and inks may change color when the apparel is heated to progressively higher temperatures above the pre-exercise, resting body shell temperature. The heat is generally supplied by skin that is in contact with or is proximal to the material of the apparel, and the body heat increases with increasing physical exertion. As the dyes and inks change color, at least a portion of the apparel also changes color. The color change reflects the temperature of the apparel at any given portion. It is preferred that the apparel comprises at least two, in some aspects at least three, and in some aspects at least four thermochromic dyes. These thermochromic dyes may change color when the apparel is heated to a temperature sufficient to melt the particular low melting wax with which the dye is mixed. The temperature of different portions of the apparel is a function of the body shell temperature most proximal to those portions, and the color of a given portion of the apparel preferably reflects the temperature of the body shell covered by that portion. The following tables illustrate non-limiting examples of apparel temperatures at which each dye or ink in a plurality may change color in accordance with an embodiment of the invention.

TABLE 1

Temperature changes for apparel comprising four thermochromic dyes or inks.

| No color change (° C.) | Color change for thermochromic dye/ink 1 (° C.) | Color change for thermochromic dye/ink 2 (° C.) | Color change for thermochromic dye/ink 3 (° C.) | Color change for thermochromic dye/ink 4 (° C.) |
|---|---|---|---|---|
| 32 | 33 | 34 | 35 | 36 |
| 32 | 33 | 34 | 35 | 37 |
| 32 | 33 | 35 | 37 | 39 |
| 32 | 33 | 36 | 38 | 40 |
| 32 | 34 | 36 | 38 | 40 |
| 32 | 34 | 35 | 36 | 37 |
| 32 | 34 | 35 | 37 | 39 |
| 32 | 34 | 35 | 37 | 38 |
| 33 | 34 | 35 | 36 | 37 |
| 33 | 34 | 36 | 38 | 40 |
| 33 | 34 | 35 | 37 | 39 |
| 33 | 34 | 35 | 36 | 38 |
| 33 | 35 | 36 | 37 | 38 |
| 33 | 35 | 37 | 39 | 40 |
| 33 | 35 | 36 | 38 | 40 |
| 34 | 35 | 36 | 37 | 38 |
| 34 | 35 | 37 | 38 | 39 |
| 34 | 35 | 37 | 39 | 40 |
| 34 | 36 | 37 | 38 | 39 |
| 34 | 36 | 38 | 39 | 40 |
| 34 | 37 | 38 | 39 | 40 |
| 35 | 36 | 37 | 38 | 39 |
| 35 | 37 | 38 | 39 | 40 |
| 35 | 36 | 38 | 39 | 40 |
| 35 | 36 | 37 | 39 | 40 |

TABLE 2

Temperature changes for apparel comprising three thermochromic dyes or inks.

| No color change (° C.) | Color change for thermochromic dye/ink 1 (° C.) | Color change for thermochromic dye/ink 2 (° C.) | Color change for thermochromic dye/ink 3 (° C.) |
|---|---|---|---|
| 32 | 33 | 34 | 35 |
| 32 | 33 | 35 | 37 |
| 32 | 33 | 37 | 39 |
| 32 | 33 | 36 | 39 |
| 32 | 35 | 37 | 40 |
| 32 | 35 | 38 | 40 |
| 32 | 34 | 35 | 36 |
| 32 | 34 | 36 | 38 |
| 32 | 34 | 37 | 40 |
| 32 | 34 | 38 | 40 |
| 32 | 34 | 36 | 39 |
| 32 | 34 | 35 | 39 |
| 33 | 35 | 36 | 37 |
| 33 | 35 | 36 | 38 |
| 33 | 35 | 36 | 39 |
| 33 | 35 | 37 | 39 |
| 33 | 35 | 37 | 40 |
| 33 | 35 | 38 | 40 |
| 33 | 36 | 37 | 38 |
| 33 | 36 | 38 | 40 |
| 33 | 36 | 37 | 39 |
| 33 | 36 | 38 | 39 |
| 33 | 37 | 38 | 39 |
| 34 | 35 | 36 | 37 |
| 34 | 35 | 37 | 39 |
| 34 | 35 | 37 | 40 |
| 34 | 36 | 38 | 40 |
| 34 | 36 | 37 | 38 |
| 34 | 36 | 37 | 39 |
| 34 | 37 | 38 | 39 |
| 35 | 36 | 37 | 38 |
| 35 | 36 | 38 | 40 |
| 35 | 37 | 38 | 39 |
| 35 | 37 | 38 | 40 |
| 35 | 37 | 39 | 40 |

TABLE 3

Temperature changes for apparel comprising two thermochromic dyes or inks.

| No color change (° C.) | Color change for thermochromic dye/ink 1 (° C.) | Color change for thermochromic dye/ink 2 (° C.) |
|---|---|---|
| 32 | 33 | 34 |
| 32 | 33 | 35 |
| 32 | 34 | 36 |
| 32 | 34 | 38 |
| 32 | 34 | 39 |
| 32 | 35 | 37 |
| 32 | 35 | 38 |
| 32 | 35 | 39 |
| 32 | 35 | 40 |
| 32 | 36 | 38 |
| 32 | 36 | 39 |
| 32 | 36 | 40 |
| 32 | 37 | 39 |
| 32 | 37 | 40 |
| 33 | 34 | 35 |
| 33 | 34 | 36 |
| 33 | 34 | 37 |
| 33 | 35 | 36 |
| 33 | 35 | 37 |
| 33 | 35 | 38 |
| 33 | 35 | 39 |
| 33 | 35 | 40 |
| 33 | 36 | 37 |
| 33 | 36 | 38 |
| 33 | 36 | 39 |
| 33 | 36 | 40 |
| 33 | 37 | 38 |
| 33 | 37 | 39 |
| 33 | 37 | 40 |
| 33 | 38 | 40 |
| 34 | 35 | 36 |
| 34 | 35 | 37 |
| 34 | 35 | 38 |
| 34 | 35 | 39 |
| 34 | 36 | 37 |
| 34 | 36 | 38 |
| 34 | 36 | 39 |
| 34 | 37 | 39 |
| 34 | 37 | 40 |
| 34 | 38 | 40 |
| 35 | 36 | 37 |
| 35 | 36 | 39 |
| 35 | 36 | 40 |
| 35 | 37 | 39 |
| 35 | 37 | 40 |
| 35 | 38 | 39 |
| 35 | 38 | 40 |

Figure 2:
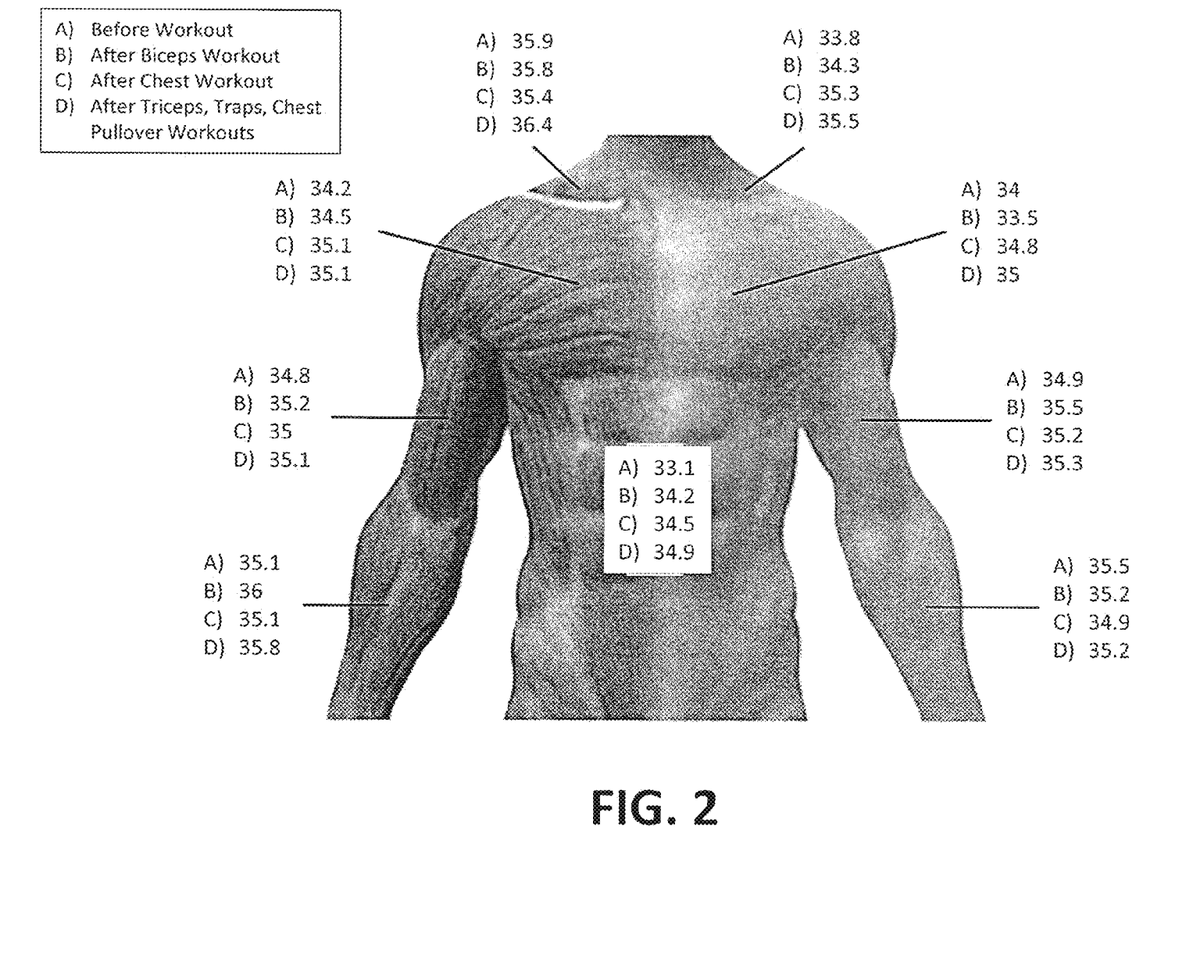
FIG. 2 diagrams the surface body temperature (in Celsius) of various regions of the torso both at rest (e.g., before workout) and after certain muscle groups are exercised.

The body shell temperature generally is not uniform, and different areas of the body may have different shell temperatures at any given time. In addition, different areas of the body may have different shell temperatures depending on which muscles or muscle groups are being exercised. See, FIG. 2. For example, when a bicep muscle on the left side of the body is being exercised, the body shell temperature at and proximal to the left bicep muscles may be greater than the body shell temperature at and proximal to the right bicep muscles if the right bicep muscles are not concomitantly being exercised, or are being exercised to a lesser degree relative to the left bicep muscles. Exercise of one muscle group, however, may result in an increase in the body shell temperature at an area of the body distal from the muscle group being exercised, for example, exercise of a bicep muscle may increase the body shell temperature at the forearm, chest, shoulder, back, and neck, among other areas.

The apparel preferably indicates optimal muscle performance, reflected in increases in the body shell temperature that heat the apparel and cause color changes from the thermochromic dyes and inks. In some aspects, the thermochromic ink changes color only at the body shell temperature that indicates peak or optimal muscle performance, such that the wearer can determine when the optimal body shell temperature has been achieved.

Figure 3A:
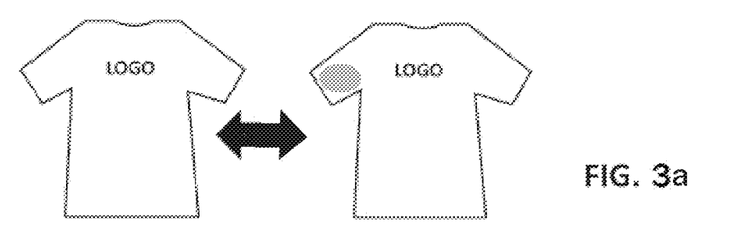
FIG. 3a diagrams a shirt color change on the sleeve of the shirt in response to changes in surface body temperature.
Figure 3B:
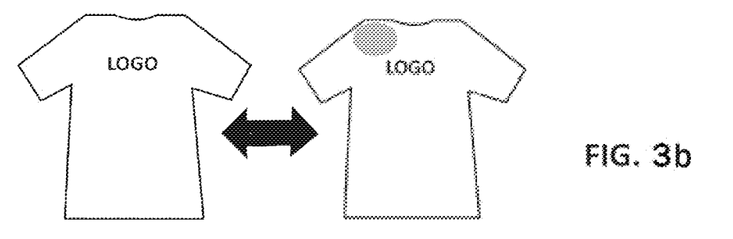
FIG. 3b diagrams a shirt color change on the shoulder of the shirt in response to changes n surface body temperature.
Figure 3C:
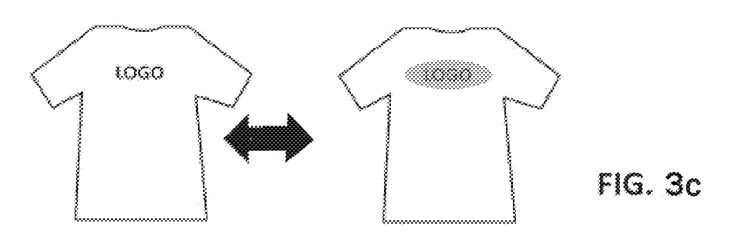
FIG. 3c diagrams a shirt color change on the chest of the shirt in response to changes in surface body temperature.

In some aspects, the apparel includes thermochromic dyes in certain portions of the apparel only, which may allow the wearer to monitor and optimize performance for a particular muscle group. Using the non-limiting example of a shirt, in some aspects, only the sleeves of the shirt may comprise a plurality of thermochromic dyes or inks, as in FIG. 3a, so that the wearer may monitor the performance of the muscles in the arm. In some aspects, the sleeves may be further subdivided according to an upper and lower portion to allow the wearer to monitor the performance of the forearm (e.g., brachioradialis, flexors, and extensors) versus performance of the upper arm (e.g., bicep). Other portions and/or subdivisions may be included. Using the shirt as an example, in some aspects, the shirt may include a plurality of thermochromic dyes or inks substantially at the shoulder portion, as in FIG. 3b, the chest portion, as in FIG. 3c, the neck portion, the upper or lower back portion, and/or the abdominal portion, in addition or in the alternative to the sleeves.

The apparel may be used to monitor and optimize muscle performance. Accordingly, the invention also features methods for monitoring muscle performance. The methods generally comprise evaluating color changes in apparel comprising a thermochromic dye. The apparel may be any apparel described or exemplified herein. The color changes arise from heating of portions of the apparel through its proximity to, including contact with, a wearer's skin, with the skin reflecting increases in the body's shell temperature caused by exercising one or more muscles.

In some aspects, the methods comprise wearing apparel comprising a plurality of thermochromic dyes, exercising one or more muscle groups beneath the apparel to a degree that increases the body shell temperature between the muscle groups and the apparel, determining the body shell temperature by detecting a change from a first color of the apparel to a second color of the apparel, and modulating the intensity of the exercise of the one or more muscle groups to a degree that increases or decreases the body shell temperature between the muscle groups and the apparel until the body shell temperature is or reflects substantially the optimal performance temperature for the one or more muscle groups. In some aspects, the determining and modulating steps may be repeated a suitable number of times until the body shell temperature is or reflects substantially the optimal performance temperature for the one or more muscle groups. In aspects where the determining and modulating steps are repeated, the determining step may comprise detecting a change from the second color of the apparel to a third color of the apparel, and may comprise detecting a change from the third color of the apparel to a fourth color of the apparel, all the way up to the number of possible colors through which the apparel may pass.

The apparel is preferably a shirt. Exercise may comprise any suitable physical activity or movement of the one or more muscle groups. Modulating may comprise increasing the intensity of the exercise or decreasing the intensity of the exercise. The degree in which the intensity is modulated can vary, and may depend on factors such as the gender, age, height, weight, or degree of physical fitness of the individual, as well as the type of exercise, and capacity to increase or decrease the intensity.

The second, third, and fourth color of the apparel each independently corresponds to a particular body shell temperature. The second, third, or fourth color may comprise the color that corresponds to the optimal performance temperature. In some aspects, the third or fourth color corresponds to a hyperthermic temperature. In some aspects, the second or third color corresponds to a sub-optimal performance temperature, e.g., a temperature below the optimal performance temperature. A sub-optimal, optimal, or hyperthermic body shell temperature corresponds to the temperature of particular muscles or muscle groups that induces heating of the skin.

The optimal performance temperature may be particular to a specific muscle or muscle group, and thus, may vary among different groups of muscles. For example, the optimal performance temperature for one muscle or muscle group may be different for the optimal performance temperature for another muscle or muscle group. Relatedly, a sub-optimal performance temperature or hyperthermic temperature for one muscle or muscle group may be the optimal performance temperature for another muscle or muscle group, and the optimal performance temperature for one muscle or muscle group may be a sub-optimal or hyperthermic temperature for another muscle or muscle group. For the torso, muscle groups include the trapezius, deltoids, pectoralis major, pectoralis minor, bicep, brachioradialis, flexors, extensors, rectus, oblique, latissiums, serratus, and teres, among other muscles of the neck, shoulder, chest, back, abdomen, and arms.

Optimal performance temperature generally is about 33° C. to about 38° C., although in some aspects, may be below about 33° C. or above about 38° C. Optimal performance temperature may be about 33° C. to about 35° C. In some aspects, optimal performance temperature is about 33° C., 34° C., 35° C., 36° C., 37° C., or 38° C. Sub-optimal performance temperature is generally about 29° C. to about 35° C., although in some aspects, may be below about 29° C. to or above about 35° C. Sub-optimal performance temperature may be about 29° C. to about 31° C., or about 29° C. to about 32° C. In some aspects, sub-optimal performance temperature is about 29° C., 30° C., 31° C., 32° C., 33° C., 34° C., or 35° C. Hyperthermic temperature generally is about 37° C. to about 40° C., although in some aspects, may be below about 37° C. or above about 40° C. In some aspects, hyperthermic temperature is about 37° C., 38° C., 39° C., or 40° C. Hyperpyrexia, a dangerous temperature condition, may be greater than about 40° C.

The apparel may be thermochromically dyed according to any suitable process. Exhaust dyeing is a preferred process. Sublimation printing may also be used to color the apparel with a thermochromic dye. Tie-dying may also be used to color the apparel with a thermochromic dye, for example, at desired portions of the apparel.

In a preferred exhaust dyeing process, the apparel is contacted with a sufficient amount of a cationic agent for a period of time sufficient to confer a charge on the fabric of the apparel; rinsed to remove excess cationic agent; contacted with a dye solution for a period of time sufficient to dye the fabric; optionally contacted with a dispersing agent for a period of time sufficient to ensure a substantially uniform amount of thermochromic dyes are coated onto the fabric; contacted with a binding agent for a period of time sufficient to bind the thermochromic dyes to the fabric; contacted with a fixing agent for a period of time sufficient to enhance the binding of the thermochromic dyes to the fabric; rinsed to remove excess dye, the binding agent, and the fixing agent; and dried. In some aspects, the apparel is dyed with a non-thermochromic dye before being subjected to a process that dyes the fabric with a plurality of thermochromic dyes.

In some aspects, the fixing agent is contacted with the fabric prior to contacting the fabric with the binding agent, and vice versa. Drying may comprise air drying, for example, at room temperature. The binding and/or the fixing agent may be tailored to a specific type of fabric, such as a binding or fixing agent for cotton or a synthetic fabric such as nylon or polyester. Drying may be enhanced by circulating air or heating the apparel.

In some aspects, a logo or design comprising one or a plurality of thermochromic inks may optionally be coated onto the apparel. The coating may be carried out according to any method suitable in the art, including screening, direct to garment, airbrushing, heat pressing inkjet transfer, and sublimation printing.

A sufficient period of time to apply the coating may comprise a period of minutes, hours, or even days. Generally, a sufficient period of time comprises about 5 minutes to about one hour, although times shorter than about 5 minutes or longer than about one hour may be employed. A sufficient period of time may comprise about 10 minutes, about 15 minutes, about 20 minutes, about 25 minutes, about 30 minutes, about 35 minutes, about 40 minutes, about 45 minutes, about 50 minutes, about 55 minutes, or about 60 minutes.

The agents, including the binding agent, thermochromic dye, dispersing agent, binding agent, and/or fixing agent may be any such agent suitable in the art. In any step in which the apparel is contacted with such an agent, the contacting may be carried out at an elevated temperature. Any contacting step may be independently carried out at a temperature of about 25° C., about 30° C., about 40° C., about 50° C., about 55° C., about 60° C., about 65° C., about 70° C., about 75° C., about 80° C., about 85° C., about 90° C., or higher.

The thermochromic dyes and non-thermochromic dyes may comprise any suitable colors, and the thermochromic dyes may change color at any desired temperature, including any temperature or temperature range described or exemplified herein. The dye solution may comprise thermochromic dyes or a mixture of thermochromic dyes and non-thermochromic dyes.

In the dye step where a thermochromic dye and non-thermochromic dye are used as the dye/colorant of the dye solution, the thermochromic dye may comprise about 30% to about 95% of the dye/colorant and the non-thermochromic dye may comprise about 5% to about 70% of the dye/colorant. The thermochromic dye may comprise about 35% to about to about 93% of the dye/colorant, and the non-thermochromic dye may comprise about 7% to about 65% of the dye/colorant. The thermochromic dye may comprise about 35% to about to about 74% of the dye/colorant, and the non-thermochromic dye may comprise about 26% to about 65% of the dye/colorant. The thermochromic dye may comprise about 35% to about to about 50% of the dye/colorant, and the non-thermochromic dye may comprise about 50% to about 65% of the dye/colorant. The thermochromic dye may comprise about 35% to about to about 43% of the dye/colorant, and the non-thermochromic dye may comprise about 57% to about 65% of the dye/colorant.

In some aspects, the thermochromic dye comprises about 35% of the dye/colorant, and the non-thermochromic dye comprises about 65% of the dye/colorant. In some aspects, the thermochromic dye comprises about 43% of the dye/colorant, and the non-thermochromic dye comprises about 57% of the dye/colorant. In some aspects, the thermochromic dye comprises about 50% of the dye/colorant, and the non-thermochromic dye comprises about 50% of the dye/colorant. In some aspects, the thermochromic dye comprises about 74% of the dye/colorant, and the non-thermochromic dye comprises about 26% of the dye/colorant. In some aspects, the thermochromic dye comprises about 93% of the dye/colorant, and the non-thermochromic dye comprises about 7% of the dye/colorant.

The dye/colorant may be diluted in a solvent, preferably an aqueous solvent such as water, to prepare the dye solution for application to the apparel. The dye/colorant may comprise about 2% to about 20% of the dye solution. The dye/colorant may comprise about 3% to about 15% of the dye solution. The dye/colorant may comprise about 5% to about 15% of the dye solution. The dye/colorant may comprise about 6% to about 12% of the dye solution. The dye/colorant may comprise about 8% to about 10% of the dye solution. The dye/colorant may comprise about 3%, about 6%, about 9%, about 10%, or about 12% of the dye solution. The dispersing agent, binding agent, and fixing agent are all preferably added to the dye solution during the process, though they are preferably added in succession.

The invention is not limited to the embodiments described and exemplified above, but is capable of variation and modification within the scope of the appended claims.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. It is also expressly intended that the steps of the methods disclosed above are not restricted to any particular order.

What is claimed:

1. Exercise apparel for monitoring optimal body shell temperature in a wearer of the apparel, comprising a first set of fibers having a first thermochromic dye infused therein that changes color at 32 degrees C., a second set of fibers having a second thermochromic dye infused therein that changes color at 34 degrees C., and a third set of fibers having a third thermochromic dye infused therein that changes color at 36 degrees C.;

and wherein the apparel is capable of showing the temperatures of portions of the wearer's body based on the color changes of the thermochromatic dyes.

2. The exercise apparel of claim 1, further comprising a logo or a design comprising a thermochromic ink that changes color at 34 degrees C.

3. The exercise apparel of claim 1, wherein the fibers comprise cotton and nylon fibers.

4. The exercise apparel of claim 1, further comprising a fourth set of fibers having a fourth thermochromic dye infused therein that changes color at 38 degrees C.

5. The exercise apparel of claim 1, wherein the apparel is a shirt.

6. The exercise apparel of claim 5, wherein the first thermochromic dye, the second thermochromic dye, and the third thermochromic dye are present only in a sleeve of the exercise apparel.

7. The exercise apparel of claim 5, wherein the first thermochromic dye, the second thermochromic dye, and the third thermochromic dye are present only on a shoulder portion of the exercise apparel.

8. The exercise apparel of claim 5, wherein the first thermochromic dye, the second thermochromic dye, and the third thermochromic dye are present only on a chest portion of the exercise apparel.

9. The exercise apparel as claimed in claim 1 wherein a portion of the fibers are moisture wicking fibers.

10. Exercise apparel for monitoring optimal body shell temperature in a wearer of the apparel, comprising a first set of fibers having a first thermochromic dye infused therein that changes color at 33 degrees C., a second set of fibers having a second thermochromic dye infused therein that changes color at 35 degrees C., and a third set of fibers having a third thermochromic dye infused therein that changes color at 37 degrees C.;
and
wherein the apparel is capable of showing the temperatures of portions of the wearer's body based on the color changes of the thermochromatic dyes.

11. The exercise apparel of claim 10, further comprising a logo or a design comprising a thermochromic ink that changes color at 35 degrees C.

12. The exercise apparel of claim 10, wherein the fibers comprise cotton and nylon fibers.

13. The exercise apparel of claim 10, wherein the apparel is a shirt.

14. The exercise apparel of claim 10, wherein the first thermochromic dye, the second thermochromic dye, and the third thermochromic dye are present only in a sleeve of the exercise apparel.

15. The exercise apparel of claim 10, wherein the first thermochromic dye, the second thermochromic dye, and the third thermochromic dye are present only on a shoulder portion of the exercise apparel.

16. The exercise apparel of claim 10, wherein the first thermochromic dye, the second thermochromic dye, and the third thermochromic dye are present only on a chest portion of the exercise apparel.

17. The exercise apparel as claimed in claim 10 wherein a portion of the fibers are moisture wicking fibers.

* * * * *